Sept. 20, 1949. H. A. M. VERSCHUREN Plant Pat. 874
ROSE PLANT
Filed Feb. 14, 1949
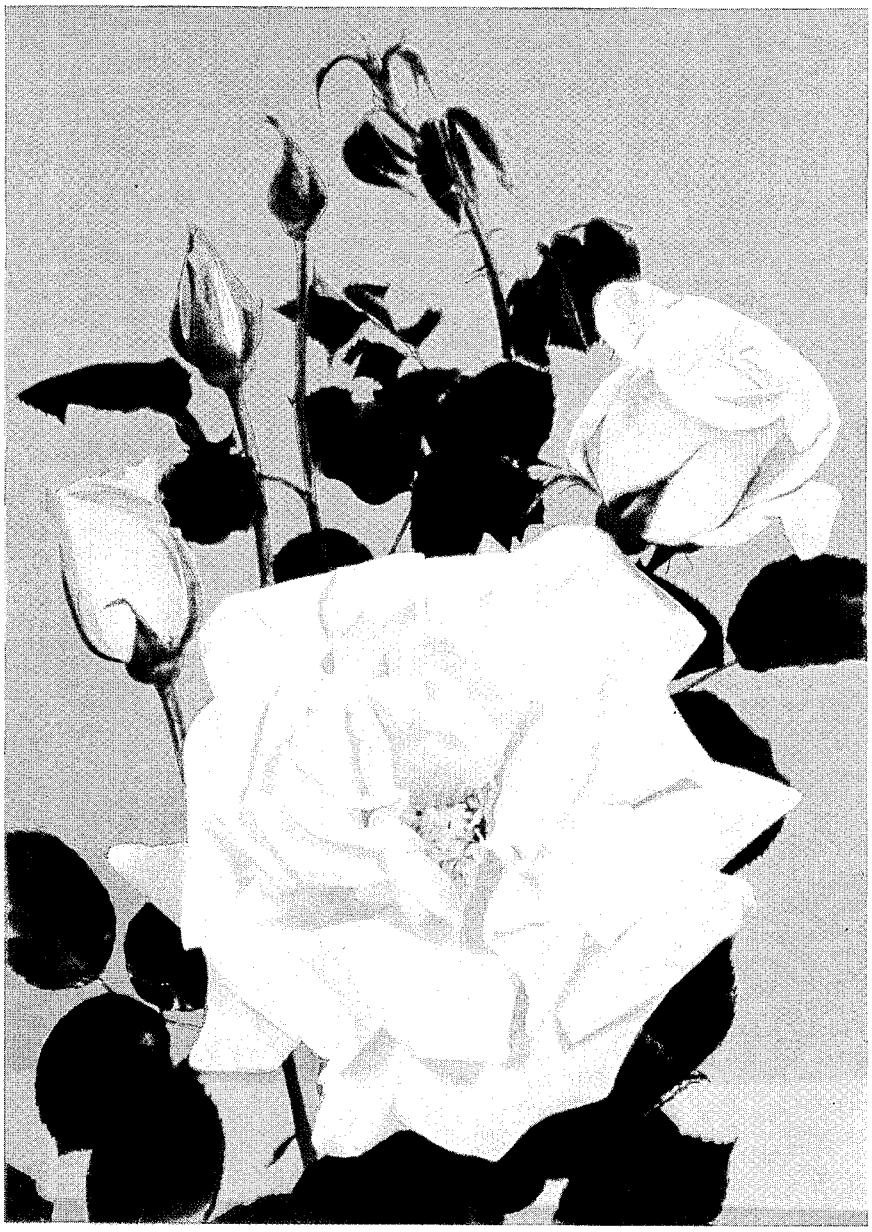
Inventor
H. A. M. Verschuren
By Robb & Robb
Attorneys Patented Sept. 20, 1949

Plant Pat. 874

UNITED STATES PATENT OFFICE

874

ROSE PLANT

Hendrikus Antonie Maria Verschuren, Haps, Netherlands, assignor to Jackson & Perkins Company, Newark, N. Y., a corporation of New York Application February 14, 1949, Serial No. 76,382

1 Claim. (Cl. 47—61)

The present invention relates to a new and distinct variety of rose plant, distinguishing from its parents or other known commercial roses by the combination of its habit of freedom of growth in the greenhouse, its immense glossy foliage, the large size and color of its blooms, and particularly the great amount of fragrance of these blooms.

In connection with the last-named characteristic, it has been noted that the fragrance of a single bloom is sufficient to scent an entire room.

This new variety was originated by crossing an unnamed seedling producing Brownish Orange flowers and another unnamed seedling of yellowish coloring, having the general characteristics of "Mev. G. A. Van Rossem" (an unpatented variety).

Asexual reproduction of this new variety shows the foregoing characteristics come true to form and are established.

In the accompanying drawing are illustrated specimens of the new variety in all stages of blooming from closed bud to full blown flowers, depicting the range of coloring during these various stages.

The following is a detailed description of the new variety, color terminology being in accordance with Ridgway's Color Standards and Nomenclature:

Parentage: Seedling.

*Seed parent.*—A Brownish Orange seedling.

*Pollen parent.*—A yellowish variety of the general characteristics of "Mev. G. A. Van Rossem."

Classification: Botanic and commercial—Hybrid tea.

*Flower*

Observations made in greenhouse at Newark, New York, in the month of November, in the afternoon.

Blooming habit: Recurrent—continuous.

Bud:

*Size.*—Large.

*Form.*—Urn. Is not affected by wet or hot weather.

*Color.*—When sepals first divide—Nopal Red, Plate 1. When petals begin to unfurl—Spectrum Red, Plate 1. When half blown — inside of petals — Flesh Ocher, Plate 14; reverse of petals—Scarlet, Plate 1, overcast with Ochraceous Salmon, Plate 15.

*Sepals.*—Slightly branched. Curl back when petals begin to unfurl. Color—inside—Light Lumiere Green, Plate 17; outside—Oil Green, Plate 5.

*Calyx.*—Shape—funnel. Size—broad. Aspect—smooth. Odor when rubbed—none. Color—Scheele's Green, Plate 6.

*Peduncle.*—Length—long. Aspect—smooth. Color—Scheele's Green, Plate 6.

*Opening.*—Bud opens up well. Is not affected by adverse weather conditions.

Bloom:

*Size.*—Large. Average size when fully expanded, 5½" to 6".

*Borne.*—Singly and several together.

*Stems.*—Long; strong.

*Form.*—When first open—cupped. Permanence—outer petals curl back and inner petals curl.

*Petalage.*—Double (full but open center). Number of petals under normal conditions, 30.

*Color.*—Center of flower—Capucine Orange, Plate 3. Outer petals—Buff Yellow, Plate 4, veined heavily and overcast with Begonia Rose, Plate 1, on three petals, and three other petals Flesh color, Plate 14. Base of petals (aiglet)—Lemon Chrome, Plate 4. Inside of petals — Capucine Orange, Plate 3. Reverse of petals—Orange Buff, Plate 3, with outer edges overcast with Bittersweet Pink, Plate 2. General tonality from a distance—Capucine Orange, Plate 3.

*Variegations.*—Some of the outer petals are veined and have a white streak through the center.

*Discoloration.*—General tonality at end of first day—Capucine Orange, Plate 3. Second day—Light Salmon-Orange, Plate 2. Third day—Orange Pink, Plate 2.

Petals:

*Texture.*—Thick; leathery. Is not affected by wet or hot weather.

*Appearance.*—Inside—velvety; outside—satiny.

*Form.*—Oval.

*Arrangement.*—Irregular. Petaloids in center—few; small.

*Persistence*—Drop off cleanly.

*Fragrance.*—Strong. Nature—"Old Rose" perfume (Centifolia).

*Lasting quality.*—On the plant and as cut flower—long.

Genital organs:

*Stamens, anthers.*—Large; many. Color—Capucine Yellow, Plate 3. Arrangement—regular around styles.

*Stamens, filaments (threads).*—Long. Color—Grenadine Red, Plate 2.

*Pollen.*—Color—Orange Buff, Plate 3.

*Styles.*—Columnar uneven length; medium length; thin.

*Stigmas.*—Color—Maize Yellow, Plate 4.

*Ovaries.*—All enclosed in calyx.

3

*Plant*

Form: Bush.
Growth: Vigorous.
Foliage: 5 leaflets.
*Size.*—Very large.
*Quantity.*—Abundant.
*Color.*—New foliage: upper side—Victoria Lake, Plate 1; under side—Oxblood Red, Plate 1. Old foliage: upper side—Dark Cress Green, Plate 31; under side—light Elm Green, Plate 17.
*Shape.*—Oval pointed.
*Texture.*—Upper side—glossy; under side—smooth. Ribs and veins—impressed.
*Edge.*—Serrated (saw toothed).
*Serrations.*—Double; small; sharp.
*Leaf stem.*—Color—Light Elm Green, Plate 17. Under side—smooth.
*Stipules.*—Medium length; smooth.
*Disease resistance.*—Resistant.

4

Wood:
*New wood.*—Color—Rainette Green, Plate 31. Bark—smooth.
*Old wood.*—Color—Bice Green, Plate 17. Bark—smooth.
Thorns:
*Quantity.*—On main stems from base and on laterals from stalk—many. Form—broad base; long; hooked down slightly. Color when young—Acajou Red, Plate 13. Position—irregular.
*Prickles and short needles.*—None.

I claim:

A new and distinct variety of rose plant, characterized as to novelty by its habit of free growth in the greenhouse, its production of very large green, glossy foliage, the large size and coloring of the flowers, and the unusual fragrance characteristic of the flowers, substantially as shown and described.

HENDRIKUS ANTONIE MARIA VERSCHUREN.

No references cited.